US012558019B2

(12) United States Patent
Várkuti et al.

(10) Patent No.: US 12,558,019 B2
(45) Date of Patent: Feb. 24, 2026

(54) BALANCE PROSTHESIS DEVICE, METHOD, SYSTEM AND COMPUTER PROGRAM

(71) Applicant: CEREGATE GMBH, Munich (DE)

(72) Inventors: Bálint Várkuti, Munich (DE); Saman Hagh-Gooie, Munich (DE)

(73) Assignee: CEREGATE GmbH, Munich (DE)

( * ) Notice: Subject to any disclaimer, the term of this patent is extended or adjusted under 35 U.S.C. 154(b) by 180 days.

(21) Appl. No.: 17/234,300

(22) Filed: Apr. 19, 2021

(65) Prior Publication Data

US 2022/0313141 A1      Oct. 6, 2022

(30) Foreign Application Priority Data

Apr. 1, 2021    (EP) ..................................... 21166577

(51) Int. Cl.
　　*A61B 5/00*　　　　(2006.01)
　　*A61B 5/11*　　　　(2006.01)
(52) U.S. Cl.
　　CPC .......... *A61B 5/4023* (2013.01); *A61B 5/0004* (2013.01); *A61B 5/1112* (2013.01);
　　　　　　(Continued)
(58) Field of Classification Search
　　CPC ... A61B 5/4023; A61B 5/1117; A61B 5/6801; A61B 5/746; A61B 2562/0219; A61B 2562/0247
　　See application file for complete search history.

(56) References Cited

U.S. PATENT DOCUMENTS 6,546,291 B2　　4/2003　Merfeld et al.
7,313,440 B2　12/2007　Miesel
　　　　　　(Continued)

FOREIGN PATENT DOCUMENTS

EP　　　0799597 A1　10/1997
EP　　　2974770 A1　　1/2016
　　　　　(Continued)

OTHER PUBLICATIONS

International Search report and Written Opinion in International Application No. PCT/EP2022/058761, mailed on Jul. 14, 2022, 20 pages.

(Continued)

*Primary Examiner* — James M Kish
*Assistant Examiner* — Laura Hodge
(74) *Attorney, Agent, or Firm* — Kowert, Hood, Munyon, Rankin & Goetzel, P.C.; Jeffrey C. Hood; Luke Langsjoen

(57) ABSTRACT

A balance prosthesis device for an individual including a sensor module configured to obtain a sensor signal indicative of a balance or equilibrium state of the individual, a processing module configured to determine at least one neurostimulation signal based at least in part on the obtained sensor signal, and a transmitter module configured to transmit the determined neurostimulation signal to a neurostimulation device of the individual. The neurostimulation signal is configured to elicit an artificial sensation in a specific sensory cortex area of the individual via directly stimulating afferent sensory axons of the central or peripheral nervous system of the individual targeting sensory neurons of the sensory cortex area not directly associated with vestibulo-cortical pathways of the individual. The elicited artificial sensation provides a balance indication to the individual in order to support, mimic, substitute or enhance the natural sense of balance of the individual.

20 Claims, 6 Drawing Sheets

Figure 1:
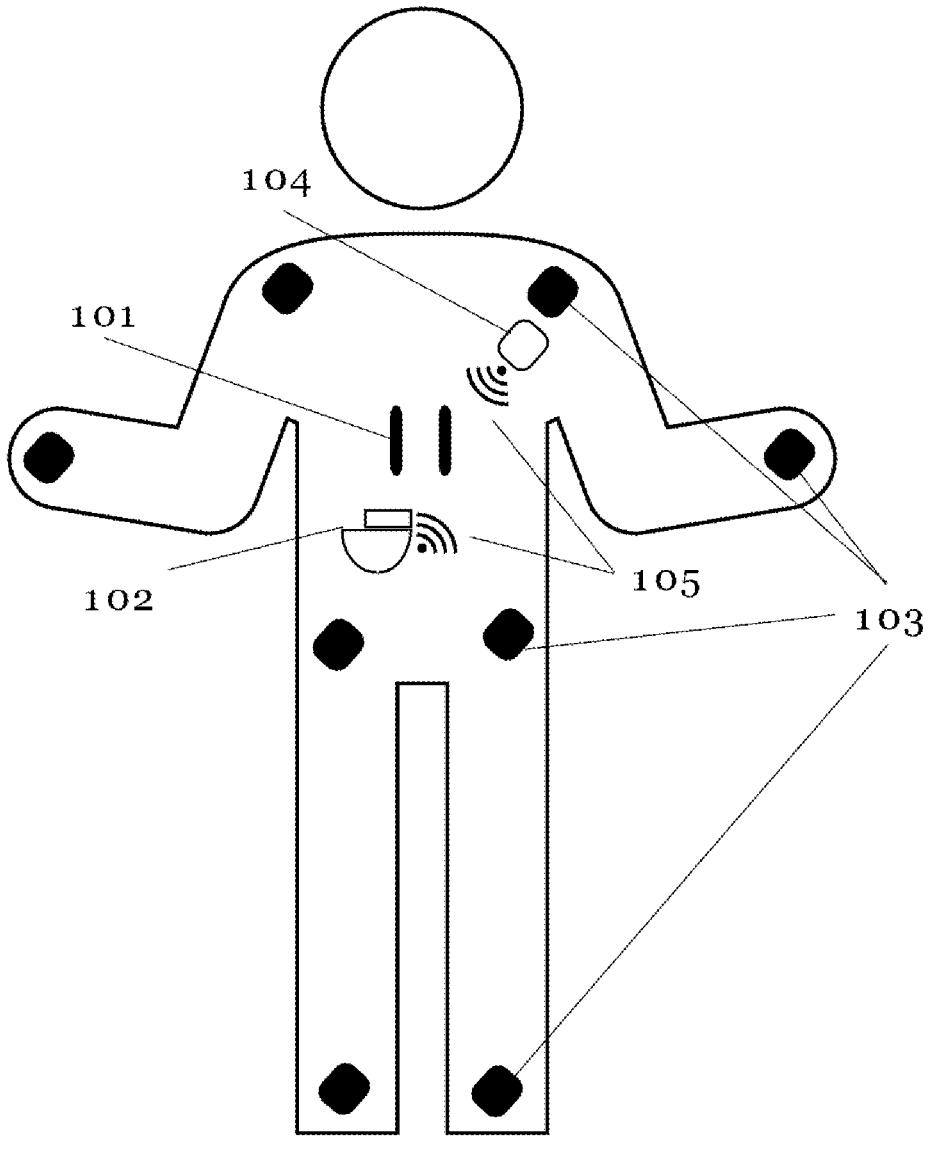

(52) U.S. Cl.
CPC .......... *A61B 5/1117* (2013.01); *A61B 5/4058* (2013.01); *A61B 5/6801* (2013.01); *A61B 5/6846* (2013.01); *A61B 5/7246* (2013.01); *A61B 5/7264* (2013.01); *A61B 5/746* (2013.01); *A61B 2562/0219* (2013.01); *A61B 2562/0247* (2013.01)

(56) References Cited

U.S. PATENT DOCUMENTS

| | | | |
|---|---|---|---|
| 7,647,120 | B2 | 1/2010 | Della Santina et al. |
| 8,702,629 | B2 | 4/2014 | Giuffrida et al. |
| 9,149,222 | B1 | 10/2015 | Zets et al. |
| 9,339,649 | B2 | 5/2016 | Cushing et al. |
| 9,974,478 | B1 | 5/2018 | Brokaw et al. |
| 10,376,739 | B2 | 8/2019 | Cook et al. |
| 2002/0010497 | A1 | 1/2002 | Merfeld et al. |
| 2007/0208403 | A1 | 9/2007 | Della Santina et al. |
| 2008/0140137 | A1 | 6/2008 | Wall, III et al. |
| 2009/0082831 | A1 | 3/2009 | Paul et al. |
| 2011/0129093 | A1 | 6/2011 | Karam et al. |
| 2012/0158094 | A1* | 6/2012 | Kramer ................ A61B 5/4082 607/48 |
| 2013/0165991 | A1* | 6/2013 | Kim ......................... A61B 5/01 607/46 |
| 2013/0261504 | A1 | 10/2013 | Claypool et al. |
| 2014/0324118 | A1* | 10/2014 | Simon .................. A61B 5/7267 607/46 |
| 2015/0032186 | A1 | 1/2015 | Cushing et al. |
| 2015/0332659 | A1 | 11/2015 | Ebeling et al. |
| 2016/0012688 | A1 | 1/2016 | Eagleman et al. |
| 2017/0113056 | A1* | 4/2017 | Stocco ..................... A61N 2/02 |
| 2017/0225033 | A1* | 8/2017 | Czaja ....................... A43B 3/34 |
| 2019/0053738 | A1 | 2/2019 | Zhang et al. |
| 2019/0344075 | A1* | 11/2019 | Bloch .................. A61B 5/4839 |
| 2020/0060602 | A1 | 2/2020 | Wagner et al. |
| 2020/0147383 | A1* | 5/2020 | Caban ................ A61N 1/36031 |
| 2020/0376272 | A1* | 12/2020 | Block ................ A61N 1/36071 |
| 2021/0170177 | A1* | 6/2021 | Minassian .......... A61N 1/36062 |

FOREIGN PATENT DOCUMENTS

| | | | | |
|---|---|---|---|---|
| EP | 3170479 | A1 | 5/2017 | |
| EP | 3381506 | A1 * | 10/2018 | .......... A61B 5/0031 |
| KR | 20190135307 | A * | 12/2019 | .............. A61B 5/11 |
| WO | 2012069429 | A1 | 5/2012 | |
| WO | 2012162658 | A1 | 11/2012 | |
| WO | WO-2015187247 | A2 * | 12/2015 | .......... A61B 5/0002 |
| WO | 2018059431 | A1 | 4/2018 | |
| WO | WO-2018109715 | A1 * | 6/2018 | .......... A61B 5/0478 |
| WO | WO-2020150737 | A1 * | 7/2020 | .......... A61M 21/02 |
| WO | 2020174051 | A1 | 9/2020 | |

OTHER PUBLICATIONS

European Search Report for European Application No. 21166577.3, mailed on Sep. 23, 2021, 4 pages.
First office action for European Patent Application No. 21166577.3, mailed on Oct. 5, 2021, 6 pages.
European Search Report issued in European Application No. 23150181.8, mailed on May 12, 2023, 8 pages.

* cited by examiner

1010

1040

1030

1050

1000

1100

BALANCE PROSTHESIS DEVICE, METHOD, SYSTEM AND COMPUTER PROGRAM

1. PRIORITY INFORMATION

This application claims priority to European Patent Application Number 21166577.3 titled "BALANCE PROSTHESIS DEVICE, METHOD, SYSTEM AND COMPUTER PROGRAM" and filed on Apr. 1, 2021, which is hereby incorporated by reference in its entirety, as though fully and completely set forth herein.

2. TECHNICAL FIELD

The present invention relates to computer brain interface devices, methods, systems and computer programs that may be used to substitute, mimic, support or enhance a person's natural sense of balance in a homologous or non-homologous manner.

3. TECHNICAL BACKGROUND

The vestibular system plays a major role in maintaining body equilibrium and balance by providing information on the motion and spatial orientation of the head in space. This is possible through existence of vestibular periphery organs in the inner ear structure on each side of the head. The balance information together with information from other senses such as vision and proprioception is relayed to higher integrative neural centers within the central nervous system via afferent sensory nerve fibers. These information enable the central nervous system to generate motor reflexes to keep body's center of gravity over its base of support e.g., an area bounded to foot soles while in standing position.

A range of neuropathologies can impact body's normal balance function via affecting peripheral or central components of the vestibular or balance-related pathways. Several acute and chronic neuropathies such as brain tumor, traumatic brain injury, neurodegenerative disease (e.g. Parkinson's Disease, Alzheimer's disease), neuromuscular abnormalities, or psychiatric disorders (e.g. anxiety) exhibit balance dysfunction and dizziness which are major factors in heightened risk of falls and gait abnormalities.

In U.S. Pat. No. 6,546,291 a wearable balance prosthesis is described that provides information indicative of a wearer's spatial orientation. The balance prosthesis includes a wearable motion sensing system and a signal processor in communication with the motion sensing system. The signal processor provides an orientation signal to an encoder. The encoder generates a feedback signal based on an estimate of the spatial orientation of the body and provides that signal to a stimulator coupled to the wearer's nervous system. For instance, the stimulator may stimulate peripheral sensory organs such as the eye, the ear or the skin. Alternatively, the nervous system is directly stimulated via a stimulation electrode stimulating one of the nerves used by a properly functioning vestibular system.

Similarly, EP2974770A1 relates to an implantable vestibular prosthesis comprising an implantable nerve stimulation device that has a sensor system, a data processor in communication with the sensor system, and a nerve stimulation system in communication with the data processor and constructed to provide electrical stimulation to at least one branch of at least one vestibulocochlear nerve.

US 2008/0140137 relates to a sensory data integration system for integrating sensory data generated by a first sensory substitution device and sensory data generated by a second sensory substitution device. The system includes a processor configured to generate an orientation signal indicative of a difference between a subject's orientation and an acceptable orientation. The orientation signal is based on the sensory data generated by the first sensory substitution device and the sensory data generated by the second sensory substitution device. For instance, a stimulator may provide electrical, tactile, auditory, or visual orientation cues. Electrical stimulation may be provided, for example, by stimulating the subject with a low ampere electrical current.

US 2020/0060602 relates to a motion analysis system that includes an image capture device, at least one accelerometer, and CPU configured to receive a first set of motion data from the image capture device related to at least one joint of a subject while the subject is performing a task and receive a second set of motion data from the accelerometer related to the at least one joint of the subject while the subject is performing the task. The CPU also calculates kinematic and/or kinetic information about the at least one joint of a subject from a combination of the first and second sets of motion data, and outputs the kinematic and/or kinetic information for purposes of assessing a movement disorder.

U.S. Pat. No. 8,702,629 B2 discloses a closed-loop deep brain stimulation system. A movement measuring device, worn by a subject, and comprising a sensor module and transceiver unit continually measures the subjects movement data. The transceiver unit correlates with a database and uses a trained algorithm to optimize a custom deep brain stimulation treatment protocol for the subject.

Similarly, U.S. Pat. No. 9,974,478 relates to systems for helping subjects improve safety and efficiency of their movements via monitoring a subject's movement to detect or predict unsafe, undesirable, or impaired movements, or symptoms of movement disorders, and also a system for providing possible treatment methods for such conditions such as providing cues or stimuli to the subject when such unsafe or undesirable movements, instabilities or symptoms are detected or predicted.

US 2009/0082831 relates to a wearable vestibular stimulation system placed inside the ear canal. Further prior art that may be relevant for understanding the technical background of the present invention is provided by U.S. Pat. No. 7,647,120, U.S. Pat. No. 10,376,739, U.S. Pat. No. 9,149,222, U.S. Pat. No. 9,339,649, WO 2018/059431, WO 2012/162658 and U.S. Pat. No. 7,313,440.

The balance support systems known from the prior art have various deficiencies. For instance, if wearable tactile transducers are employed (e.g. see U.S. Pat. No. 6,546,291) for assisting a patient with deteriorated sense of balance the number of transducers that are required scales with the specificity of the sensory feedback. Thus, such wearable transducer systems are bulky and expensive and have a large power consumption in particular when precise balance feedback is desired. Moreover, such tactile transducers and any other kind of balance feedback that is administered via the natural sensory organs of a patient only work if the sensory organs are healthy. In addition, if multi-sensory balance feedback is desired different types of transducers (tactile, visual, auditory etc.) have to be integrated into a single balance support system, which further increases complexity, cost and power consumption.

Moreover, direct sensory substitution via electro-stimulation of the vestibular system only works if the vestibular system is only partially impaired, e.g. if only the receptor cells of the vestibular sensory organ within the inner ear are impaired but the remaining part of the vestibular nervous system is intact. Such an approach may thus fail if the impairment is located upstream in the vestibular sensory pathway, e.g. in the brainstem. Thus, for many patients direct sensory substitution of the vestibular system is not a preferred treatment option. In addition, in most cases, patient will not have suitable neurostimulation equipment already implanted that can be used to stimulate the vestibular system. Accordingly, for such a treatment implantation of dedicated stimulation electrodes or similar interface devices may be required.

It is thus a problem underlying the present invention to at least partially overcome some of the deficiencies of conventional balance supports systems outlined above.

4. SUMMARY OF THE INVENTION

The above-mentioned problems are at least partially solved by a balance prosthesis device, method and computer program as specified by the independent claims. Exemplary embodiments of the present invention are specified in the dependent claims.

Generally, the present invention allows to implement a novel closed-loop approach to restore or enhance a person's sense of balance. This approach is based on direct neurostimulation of afferent sensory axons (e.g. thalamocortical axons, afferent sensory axons of the brain stem or spinal cord and/or afferent sensory axons of the peripheral nervous system) targeting directly or indirectly (i.e. via multi-synaptic afferent pathways) sensory neurons in a specific sensory cortex area to with highly specific, fine-grained and multi-dimensional balance feedback information.

More specifically, the present invention provides a balance prosthesis device for an individual, comprising: a sensor module (or receiver module) configured to obtain at least one sensor signal indicative of a balance or equilibrium state of the individual; a processing module operably connected to the sensor module and configured to determine at least one neurostimulation signal based at least in part on the obtained sensor signal; and a transmitter module operably connected to the processing module and configured to transmit the determined neurostimulation signal to a neurostimulation device of the individual; or a neurostimulation module operably connected to the processing module, wherein the neurostimulation signal is configured to elicit an artificial sensation/sensory perception in a specific sensory cortex area of the individual via directly stimulating afferent sensory axons of the central or peripheral nervous system of the individual targeting sensory neurons of the sensory cortex area not directly associated with vestibulocortical pathways of the individual; and wherein the elicited artificial sensation provides a balance indication to the individual that is derived at least in part from the obtained sensor signal in order to support, mimic, substitute or enhance the natural sense of balance of the individual.

The various modules of the devices and systems disclosed herein can for instance be implemented in hardware, software or a combination thereof. For instance, the various modules of the devices and systems disclosed herein may be implemented via application specific hardware components such as application specific integrated circuits, ASICs, and/or field programmable gate arrays, FPGAs, and/or similar components and/or application specific software modules being executed on multi-purpose data and signal processing equipment such as CPUs, DSPs and/or systems on a chip (SOCs) or similar components or any combination thereof. For instance the various modules of the balance prosthesis device discussed above may be implemented on a multi-purpose data and signal processing device configured for executing application specific software modules and for communicating with various sensor devices and/or neurostimulation devices or systems via conventional wireless communication interfaces such as a NFC, a WIFI and/or a Bluetooth interface.

Alternatively, the various modules of the balance prosthesis device discussed above may also be part of an integrated neurostimulation apparatus, further comprising specialized electronic circuitry (e.g. neurostimulation signal generators, amplifiers etc.) for generating and applying the determined neurostimulation signals to a neurostimulation interface of the individual (e.g. a multi-contact spinal cord stimulation electrode, a deep brain stimulation (DBS) electrode, a peripheral sensory nerve stimulation electrode etc.).

The neurostimulation signals generated by the balance prosthesis device described above may for instance also be transmitted to a neuronal stimulation device comprising a signal amplifier driving a multi-contact DBS electrode, spinal cord electrode, etc. that may already be implanted into a patient's nervous system for a purpose different than providing a balance indication. Alternatively, dedicated DBS-like electrodes or spinal cord stimulation electrodes may be implanted for the purpose of applying the neurostimulation signals generated by the balance prosthesis device via established and approved surgical procedures that were developed for implantation of conventional DBS electrodes or spinal cord stimulation electrodes etc. Further, as mentioned above the balance prosthesis device may also be integrated together with a neuronal stimulation device into a single device.

It is important to note that the balance indication that is communicated by the artificial sensory perception elicited by the neurostimulation signal differs from mere sensory substitution. As will be explained in detail below any kind of abstract information that can be used to substitute, mimic, support or enhance a person's natural sense of balance can be transmitted to the individual with a balance prosthesis device according to the present invention. For instance, different neurostimulation signals may be configured to elicit different specific artificial sensory perceptions (e.g. a touch sensation in the left hand, the lower back, etc.) having different characteristics (e.g. different intensities, frequencies or secondary sensory qualities such as a texture pitch, timbre, color etc.). As will be explained in more detail below, the balance prosthesis device provided by the present invention may then be calibrated such that the different characteristics of the elicited artificial sensory perceptions indicate different balance indications such as a degree and/or a direction of a body tilt, an inclination angle of a walking surface, a predictive falling warning, etc.

The present invention also provides a method for providing a balance indication to an individual, comprising the following steps: obtaining at least one motion sensor signal indicative of a balance or equilibrium state of the individual; determining at least one neurostimulation signal based at least in part on the obtained sensor signal; and transmitting the determined neurostimulation signal to a neurostimulation device or module of the individual, wherein the neurostimulation signal is configured to elicit an artificial sensation in a specific sensory cortex area of the individual via directly stimulating afferent sensory axons of the central or peripheral nervous system of the individual targeting sensory neurons of the sensory cortex area not associated with the natural sense of balance of the individual and wherein the elicited artificial sensation provides a balance indication to the individual that is derived at least in part from the obtained motion sensor signal in order to support, mimic, substitute or enhance the natural sense of balance of the individual.

The present invention also provides a computer program, comprising instructions for carrying out the method described above, when being executed by the signal processing and transceiver modules of a signal and data processing device, a neuronal stimulation device or system.

Further, the sensor module may be configured to obtain at least one motion sensor signal via a wired or wireless interface, such as an accelerometer or a gyroscope signal; Additionally or alternatively, the sensor module may also comprise a motion sensor such as an accelerometer or a gyroscope (see FIG. 8 below). Further, the sensor module may be configured to obtain, via a wired or wireless interface, an auxiliary sensor signal originating from an auxiliary sensor device such as a camera, a LIDAR sensor, a GPS system, a pressure sensor or an elevation sensor, etc.

Further, in some embodiments of the present invention the processing module may be configure to determine, based at least in part on the obtained sensor signal, an estimate of the current body position of the individual with respect to a reference body position and/or an estimate of a future body position with respect to the reference body position.

For instance, the body position of the individual may be characterized by one or more of the following parameters: a body tilt of the individual in the coronal and/or the sagittal plane; a rate of change of the body tilt of the individual in the coronal and/or the sagittal plane, a deviation of the center of gravity of the body of the individual from a reference position or range for the center of gravity and a rate of change of the deviation of the center of gravity from the reference position or range.

In this way the balance prosthesis device provided by the present invention is enabled to determine and transmit highly specific balance indications directly to the brain of the individual. As mentioned above the neurostimulation signal may be determined based on processed input data from multiple sensors such as acceleration sensors, gyroscopes video cameras, pressures sensors and LIDAR sensors etc. The processed information may then be utilized to trigger neurostimulation by activating appropriate perceptual/sensory communication channels. In this manner, the present invention allows the use accurately timed message blocks that provide effective and automatic sensory feedback cues to the individual to substitute, mimic, support or enhance the natural sense of balance of an individual.

Further, the balance prosthesis device described above may be further configured to access a data storage device storing a plurality of relations, specific for the individual, associating a plurality of neurostimulation signals with a plurality of corresponding homologous or non-homologous balance indications or auxiliary balance support information. In some embodiments, the balance prosthesis device may also include the data storage device storing the plurality of relations.

For instance, the data storage device may contain a personalized communication library for the individual, the library storing the relations between a plurality of different balance indications or auxiliary balance support information and a plurality of corresponding neurostimulation signals. Such a stimulation signal library can be calibrated for each individual through neuroimaging and/or individualized testing of the individual. Neuroimaging may first be used to identify theoretically possible ranges of activation for an individual stimulation electrode while individualized testing determines which points in the parameter space of neurostimulation signal parameters can be perceived and decoded by the cortex of the individual. It should be emphasized that conscious individualized testing of an individual is merely one specific example of how to generate the individualized relations stored in the memory. In other embodiments such relations may also be obtained from unconscious patients, e.g. through the non-invasive observation of corresponding functional MRI responses on the somatosensory cortex or EEG recordings.

Further, once the communication library is established or while it is being established for an individual a specific training procedure can be executed that links a specific artificial sensory perception to the corresponding homologous or non-homologous balance indication. As long as the cortex of the individual responds to classical conditioning, pair learning can be executed. In the context of the present invention, such a pair consists of a given artificial sensory perception corresponding to a given neurostimulation signal and the corresponding balance indication or auxiliary balance support information to be associated with said given artificial sensory perception and the corresponding neurostimulation signal.

Importantly, the type of information to be conveyed via the balance prosthesis device described above whether it is a balance indication or similar information can be chosen more or less freely. Any information or message which can be broken down into message blocks (i.e. pieces of conceptual information that can be decoded by the cortex of an individual) can be transmitted. This includes (quasi-) continuous balance indications such as a (quasi-) continuous indication of a desired compensatory body movement or other information that may be relevant for maintaining once balance (e.g. a contact pressure difference across a foot of the individual, an inclination angle of a walking surface etc.).

In particular, the specific relations may be based at least in part on one or more of the following: conceptual or perceptual learning data for the individual, neuro-imaging data for the individual, electrophysiological measurement data for the individual, neuronal connectivity information for the individual, electric field simulation data for the employed neurostimulation interface and neuronal excitability model data for the individual.

In this way, even complex balance indications (see FIG. 5 discussed in section 5. below) can be associated with corresponding artificial sensory perceptions that are specific for each individual.

In particular, the neurostimulation signal may also be configured to stimulate afferent sensory axons of the spinal cord, the brain or the peripheral nervous system projecting directly (i.e. via a monosynaptic pathway) or indirectly (i.e. via a multi-synaptic pathway) to the thalamus or the cortex. For instance, if the neurostimulation signal is to be applied via a conventional spinal cord stimulation electrode the signal parameters of the neurostimulation signal may be adjusted such that action potentials are elicited in specific sub-populations of afferent sensory nerve fibers of the spinal cord, e.g. in a set of axons projecting via multiple synapses to somatosensory neurons in a specific sensory cortex area.

In general, the sensational modality, location, type, and intensity of the artificial sensory perception that is elicited in the cortex in response to these afferent action potentials can be controlled via precise electrode location and selection of neurostimulation parameters. The present invention uses such artificial sensations to transmit information directly to the brain in form of discrete or continuous message blocks by forming the desired perceptual channel. The perceptual channels may be established via a single or via multiple electrical contacts of a spinal cord stimulation electrode, a peripheral stimulation electrode and/or a DBS electrode which are electrically activated with calibrated neurostimulation parameters to deliver specific sensory messages to the individual. The sensation modality of the respective perceptual channel may include tactile, proprioceptive, visual, or auditory sensations based on the application or location and orientation of the implanted stimulation electrode.

For instance, perceived laterality or location of the elicited artificial sensation may indicate (e.g. in a homologous manner) a direction of a body tilt of the individual or a direction of a compensatory movement to decrease the body tilt and/or a perceived intensity of the elicited artificial sensation may encodes an angle or a degree of a body tilt of the individual relative to a reference position or range or an angle or degree of a compensatory movement to decrease the body tilt.

Using such a homologous encoding scheme (for examples see also FIG. 2, FIG. 3 and FIG. 4 discussed in section 5 below) ensures that the balance indications provided by the balance prosthesis device can intuitively understood by the individual without much adaptation or learning necessary. Thus, quick and easy acceptance of the prosthesis device may be facilitated which may be particularly desirable for mentally impaired patients.

Further, e.g. in a non-homologous manner, the perceived repetition rate of the elicited artificial sensation may encode a terrain characteristic such as an inclination angle of a walking surface the patient is walking on or a remaining distance to an obstacle. Such secondary balance indications may for example be derived from video camera or LIDAR sensor signals and/or from pressure sensors measuring the contact pressure of the feet of the individual with the walking surface.

Further, a secondary sensory quality of the elicited artificial sensation such as the texture of a somatosensation, the color of a visual sensation or the tone, pitch or timbre of an auditory sensation may encode body balance support information/secondary balance indications such as an inclination of a walking surface or a remaining distance to an obstacle.

In this manner, the natural sense of balance of an individual cannot only be substituted, mimicked, or supported but even enhanced to integrated sensory information that would not be accessible even to a healthy individual.

To improve safety during operation, the processing module of some embodiments may be configured to detect, based at least in part on the obtained motion sensor signal and/or the auxiliary sensor signal, preferably by using a trained machine learning system, whether the body of the individual is at risk to fall and in response to said detection: to generate a neurostimulation warning signal that is configured to elicit an artificial sensation in a specific sensory cortex area providing a falling warning to the individual.

In addition, the neurostimulation signal may be synchronized with a walking pace of the individual to provide a continuous body tilt correction indication improving the gait stability of the individual while walking.

In a further aspect, the present invention provides a balance prosthesis system, comprising one of the balance prosthesis devices discussed above; and one or more implanted or wearable motion sensors providing input signals to the sensor module of the balance prosthesis device. Such a system may for example include one or more of the following sensor devices providing further input signals to the sensor module of the balance prosthesis device: a camera device, a LIDAR sensor device, a GPS system/receiver, a pressure sensor measuring the contact pressure between a foot of the individual and a walking surface and/or at least two pressure sensors measuring the difference in contact pressure between two points on a walking surface to determine an inclination of the walking surface.

In some particularly advantageous embodiments, the balance prosthesis system may comprise a spinal cord stimulation device comprising a set of implanted spinal cord leads targeting somatosensory ganglions or afferent sensory nerve fibers within or adjacent to the spinal cord.

The present invention can also be used to enhance or reinforce the natural sense of balance of an individual. For instance, artificial sensory perceptions encoding a reinforcing balance indication may help to resolve perceptual conflicts between the natural sense of balance and visual perception and thereby help to overcome motion sickness (see FIG. 9 below).

In addition the present invention also provides a remote balance sensing device for an individual, comprising: a sensor module (or receiver module) configured to obtain at least one sensor signal indicative of a balance or equilibrium state of a remote moving object; a processing module operably connected to the sensor module and configured to determine at least one neurostimulation signal based at least in part on the obtained sensor signal; and a transmitter module operably connected to the processing module and configured to transmit the determined neurostimulation signal to a neurostimulation device of the individual; or a neurostimulation module operably connected to the processing module, wherein the neurostimulation signal is configured to elicit an artificial sensation in a specific sensory cortex area of the individual via directly stimulating afferent sensory axons of the central or peripheral nervous system of the individual targeting sensory neurons of the sensory cortex area not directly associated with vestibulocortical pathways of the individual; and wherein the elicited artificial sensation provides a balance indication for the remote moving object to the individual that is derived at least in part from the obtained sensor signal.

Such a remote balance sensing device may provide an individual, e.g. pilot remotely controlling, e.g. via a brain-computer interface, a drone, car, ship robot etc. with an artificial balance perception for the remote object thereby substantially improve the individual's performance in controlling the movement of the remote moving object.

5. SHORT DESCRIPTION OF THE FIGURES

Figure 2:
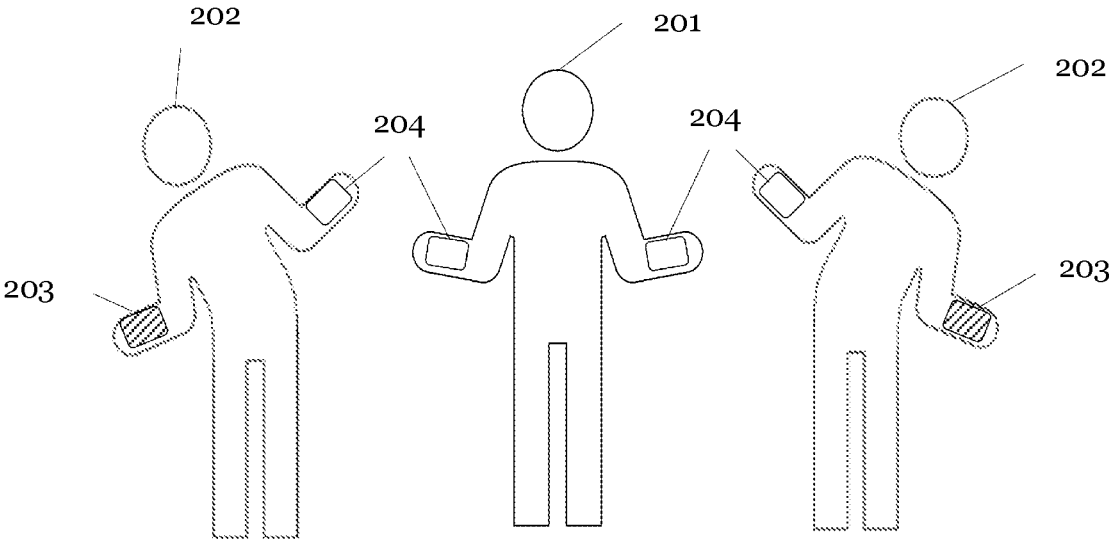
Figure 3:
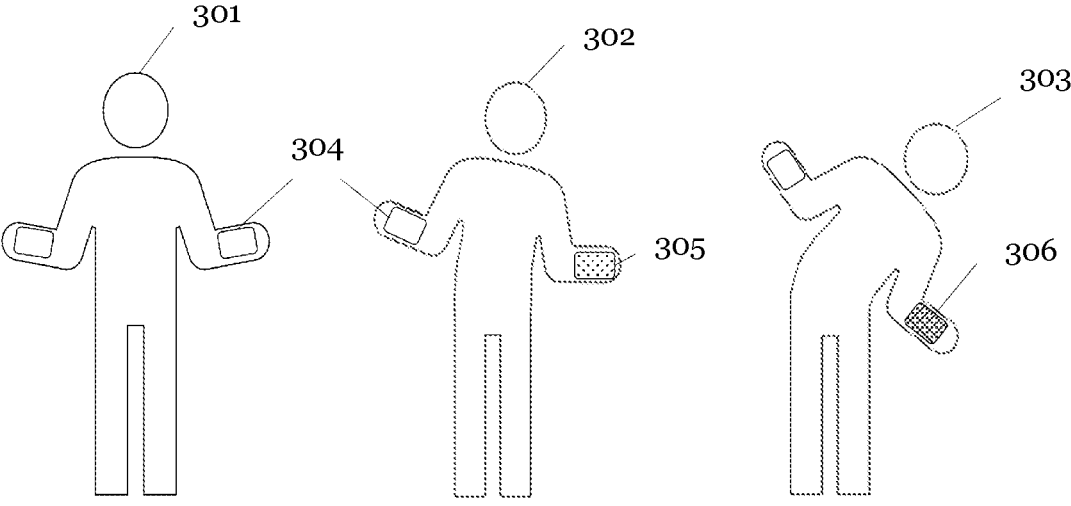
Figure 4:
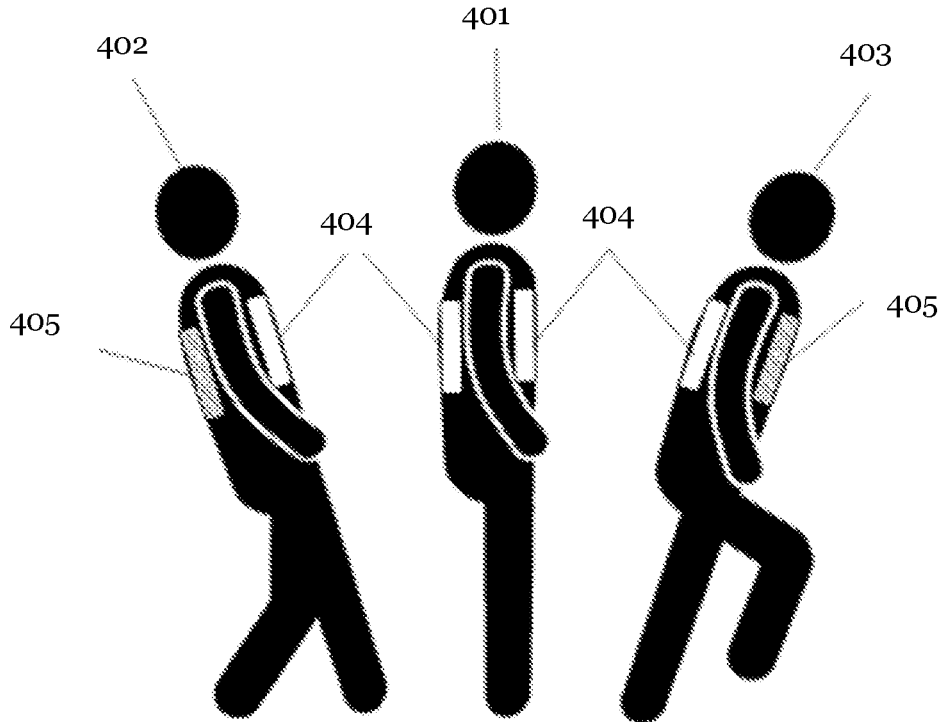
Figure 5:
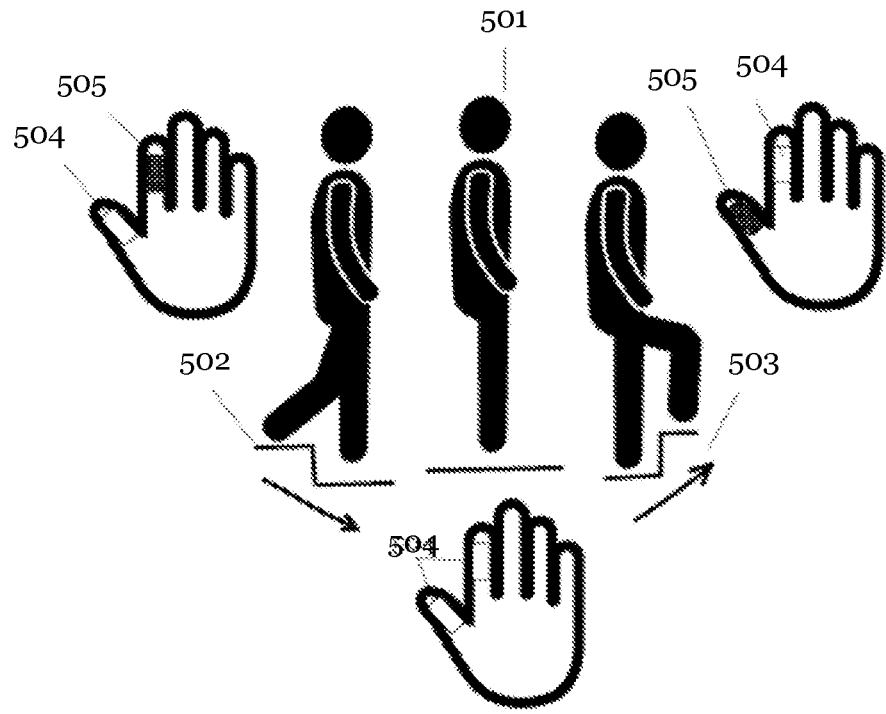
Figure 6:
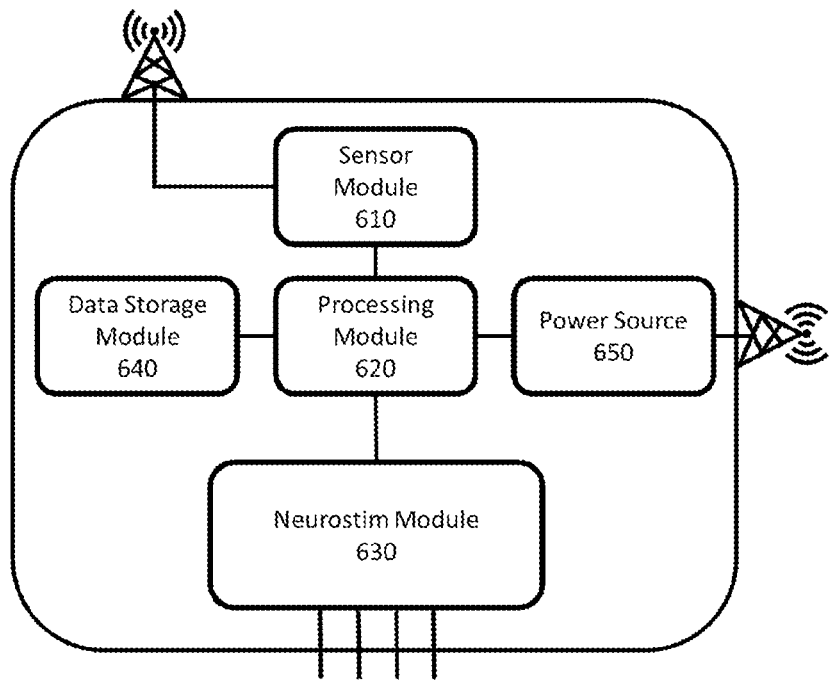
Figure 7:
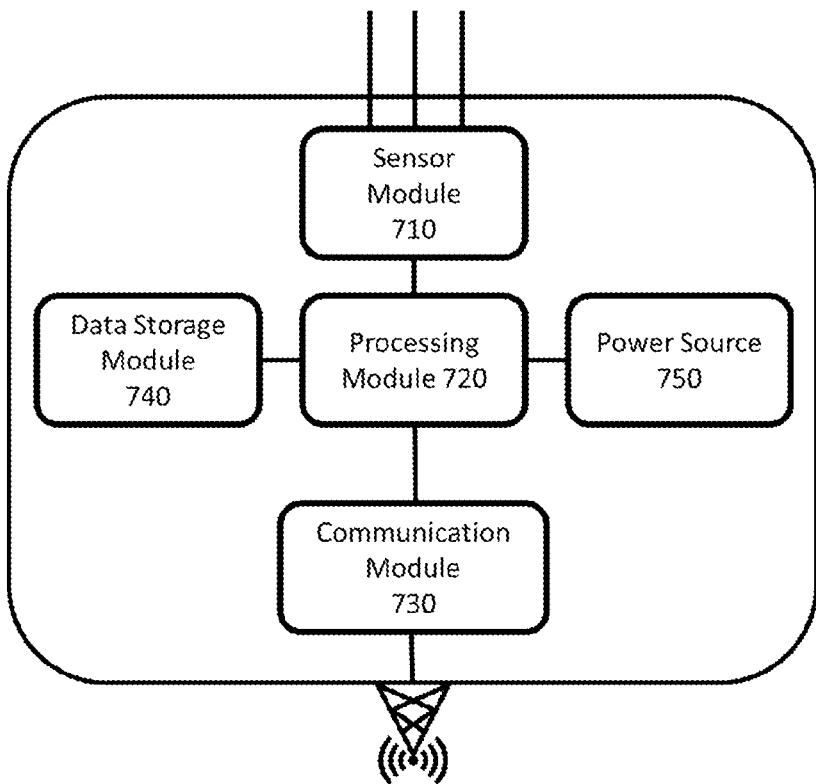
Figure 8:
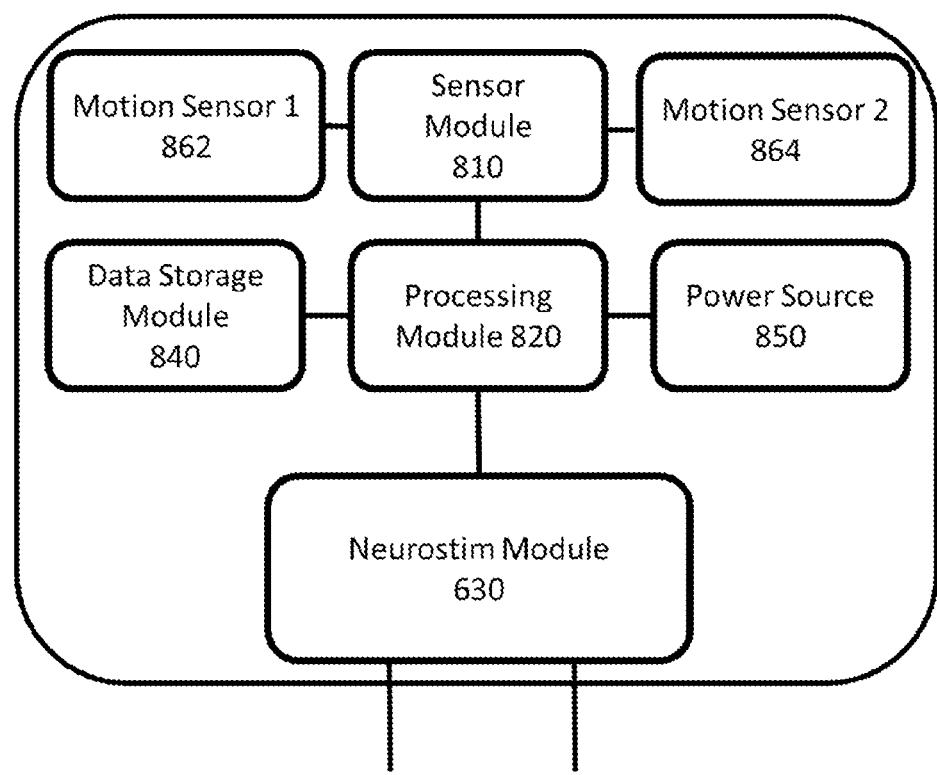
Figure 9:
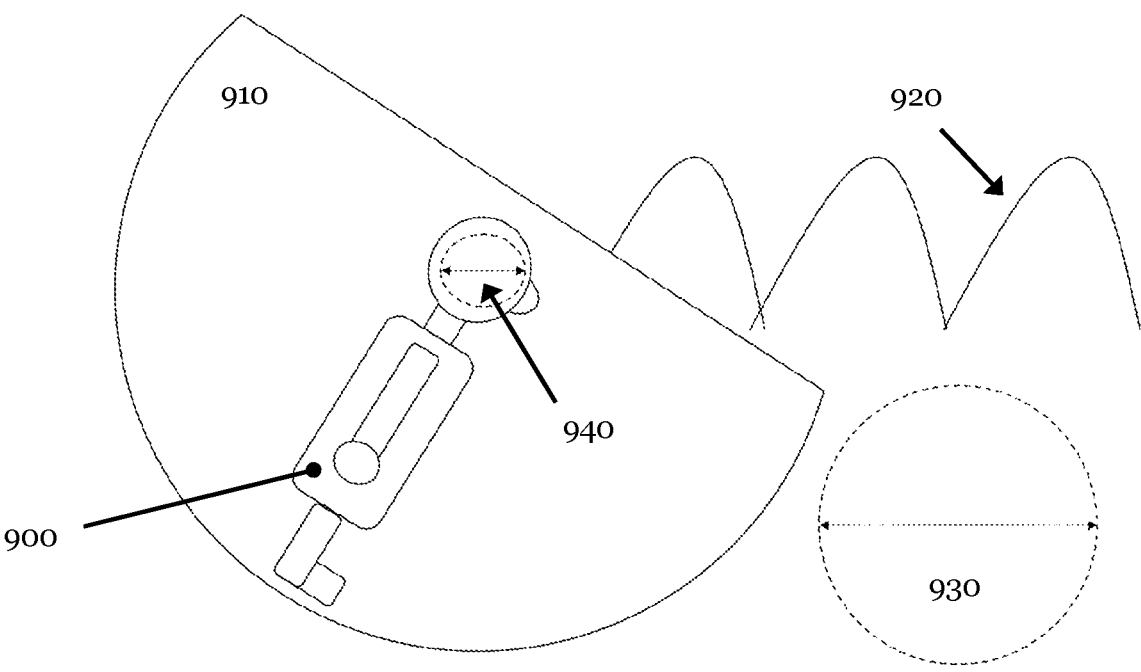
Figure 10:
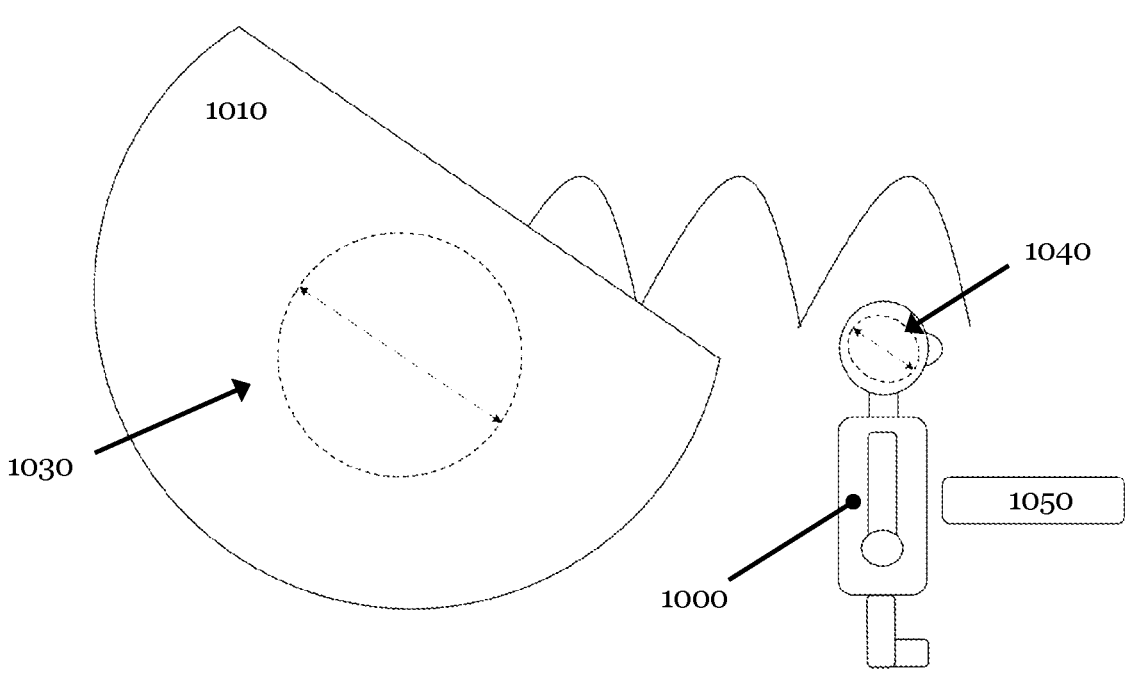
Figure 11:
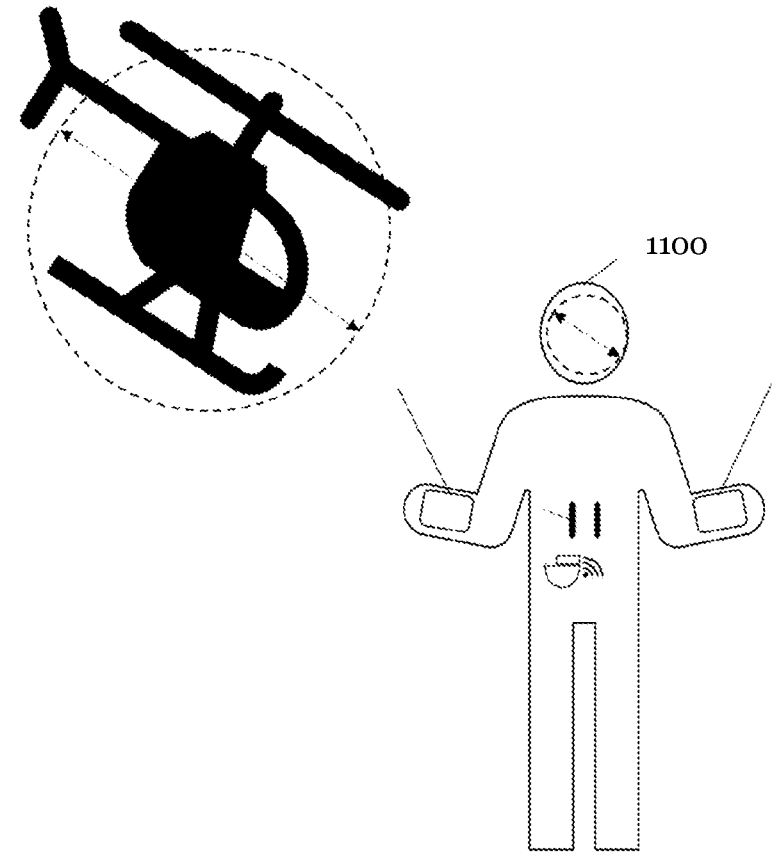

Various aspects of the present invention are described in more detail in the following by reference to the accompanying figures. These figures show:

FIG. 1 a diagram illustrating an individual being equipped with a balance prosthesis device and system comprising said device according to an embodiment of the present invention;

FIG. 2 a diagram illustrating how a homologous balance indication can be encoded using a balance prosthesis device according to an embodiment of the present invention;

FIG. 3 a further diagram illustrating how a homologous balance indication can be encoded using a balance prosthesis device according to an embodiment of the present invention;

FIG. 4 a further diagram illustrating how a homologous balance indication can be encoded using a balance prosthesis device according to an embodiment of the present invention;

FIG. 5 a diagram illustrating how a non-homologous balance support information can be encoded using a balance prosthesis device according to an embodiment of the present invention;

FIG. 6 a functional block circuit diagram illustrating a balance prosthesis device according to an embodiment of the present invention;

FIG. 7 a functional block circuit diagram illustrating a balance prosthesis device according to another embodiment of the present invention;

FIG. 8 a functional block circuit diagram illustrating a balance prosthesis device with integrated motion sensors according to another embodiment of the present invention;

FIG. 9 a diagram illustrating how a balance prosthesis device according to an embodiment of the present invention can be used to mitigate motion sickness;

FIG. 10 a diagram illustrating the operation of a remote balance sensing device according to a further aspect of the present disclosure;

FIG. 11 a further diagram illustrating the operation of a remote balance sensing device according to a further aspect of the present disclosure.

6. DETAILED DESCRIPTION OF SOME EXEMPLARY EMBODIMENTS

In the following, some exemplary embodiments of the present invention are described in more detail, with reference to a balance prosthesis device that can be interfaced with neuronal stimulation electrodes such as spinal cord stimulation electrodes, DBS electrodes and/or peripheral axonal stimulation electrodes, e.g. via an intermediate neuronal stimulation device. However, the present invention can also be used with any other neuronal stimulation interface that is capable of stimulating afferent sensory axons of the central or peripheral nervous system targeting a sensory cortex area of an individual.

While specific feature combinations are described in the following with respect to the exemplary embodiments of the present invention, it is to be understood that not all features of the discussed embodiments have to be present for realizing the invention. The disclosed embodiments may be modified by combining certain features of one embodiment with one or more features of another embodiment if technically feasible and functionally compatible. Specifically, the skilled person will understand that features, components and/or functional elements of one embodiment can be combined with technically compatible features, components and/or functional elements of any other embodiment of the present invention which is defined by the appended claims.

FIG. 1 depicts an individual 100, e.g. patient with impaired natural sense of balance that is equipped with a balance prosthesis system according to an embodiment of the present invention. The individual 100 has already been implanted (e.g. for pain management) with a pair of spinal cord stimulation electrodes 101 that may have multiple independently controllable electric contacts. In other configurations, a neuronal stimulation electrode may also be implanted into the brain of the individual 100 for the purpose of providing a neuromodulation therapy, e.g. for treating PD symptoms. Such a neurostimulation electrode may also be implanted for other purposes such as for the purpose of neuronal communication and/or treatment of other movement impairments and neurological diseases such as Alzheimer's disease, epilepsy, depression, etc. Alternatively, the electrode 101 may also be implanted as a dedicated neurostimulation interface for the balance prosthesis device and system provided by the present invention.

The balance prosthesis system shown in FIG. 1 includes an array of motion sensors 103 such as acceleration sensors or gyroscopes distributed on the body of the individual 100 e.g. through a wearable enclosure. Alternatively or additionally, similar motion sensors can also be integrated within an implanted neurostimulation device 102 such as an implantable pulse generator (IPG) that drives the spinal cord stimulation electrodes 101. The motion sensors 103 may continuously relay positional information to a balance prothesis device 104 according to some embodiments of the present invention. In other embodiments, the balance prothesis device 104 or its functions may also be integrated with the implanted neurostimulation device 102. The processing circuitry of the balance prosthesis device 104 calculates various parameters including the level of body orientation with regard to a reference set of parameters based on the body's upright position.

The balance prosthesis device 104 is wirelessly linked 105 to an implanted stimulator 102. The balance prosthesis device 104 can therefore functionally trigger the stimulator and adjust the stimulation parameters in terms of amplitude, frequency, pulse-width, burst duration and other parameters determined through a calibration process. The neurostimulator 102 is linked to a pair of implanted spinal cord leads 101 targeting somatosensory ganglions or afferent sensory nerve fibers within or adjacent to the spinal cord. The balance prosthesis device 104 receives as input a set of motion sensor signals and after processing, determines which contacts on the implanted spinal cord leads shall become active. The processor also determines a set of most suitable parameters which are most relevant to determine the location while encoding the desired type, locality and/or intensity of the artificial sensory perception that is to be elicited as discussed in detail in section 3 above.

FIG. 2 illustrates exemplary scenarios in which the system is expected to activate/elicit artificial sensory perception on different body locations (e.g. left and right hand) to encode the deviations from the body's upright equilibrium position 201 within the mediolateral plane. When the body is wayed to the left or right side 202, the ipsilateral perceptual channels 203 become active. In this way, the activation patterns of the perceptual channels provide a remedy for a totally lost or a compromised vestibular function. Patients can learn to associate the sensory cues into useful sensory input substituting, mimicking, supporting or even enhancing natural sense of balance and in response perform functionally relevant actions such as maintaining body equilibrium even when walking, running, cycling etc. In an alternative embodiment, the activation pattern of the perceptual channels could be adjusted in a reverse manner that is contralateral to the tilt side. This mode would provide necessary cues resembling compensatory muscle reflexes which are naturally situated contralateral to direction of the tilt e.g. muscle contractions on the left side when body is leaning towards the right-hand side etc.

FIG. 3 illustrates an embodiment where the intensity of the perceptual channel is used to encode the degree of body tilt. In the upright body position 301, both perceptual channels are silent and the subject does not feel anything. In a moderate tilt position 302 of, e.g. 10 degrees to the left side, the ipsilateral perceptual channel 305 is activated with calibrated neurostimulation parameters eliciting a weak artificial sensation. In a more extreme case 303 the same perceptual channel is activated but stimulation parameters are adjusted so that they cause an intense somatosensations 306 thereby alerting the subject of an eminent fall prompting the user for an immediate corrective action.

To complement the balance prosthesis device and system provided by the present invention, additional information regarding body state or other environmental variables could be integrated using various sensors and other types of transducers. Typical balance systems must contain a minimum set of two independent orthogonal motion detection axes (i.e. back-front & left-right) to achieve a simple, upright balance feedback. In the present invention, the balance information in these additional planes could be achieved via a positional feedback system rendering information from both the coronal plane (as described in FIG. 2 and FIG. 3) as well as sagittal plane (as illustrated in FIG. 4.

In FIG. 4 reference sign 401 corresponds to an upright body position, 402 to a leaned back body position and 403 to a leaned forward body position. Reference sign 404 indicates non-activated perceptual channels of the balance prosthesis system and 405 the activated perceptual channels providing a balance indication to the individual to substitute, mimic, support or enhance the natural sense of balance of the individual in a homologous manner.

In other preferred embodiments, further sensor information can be converted and integrated into the system including but not limited to a LIDAR sensor signal obtained from a LIDAR sensor such as a neck-worn personal phone, GPS-and map-position information, elevation sensor information from a wrist-worn smartwatch and others. This additional information is either utilized to optimize the position/balance-corrective cues in an intelligent manner (i.e. optimizing the resulting balance-gain outcome) or alternatively, is presented as additional one- or multi-dimensional balance-correcting axes. Consequently, a set of separate perceptual channels corresponding to artificial sensory perceptions felt in separate parts of body (or even within the same body region but with a separate quality of sensation) could be reserved to communicate specific balance support/auxiliary information to the individual.

The examples discussed above constitute essentially homologous embodiment of the present invention. For instance, the artificial sensations depicted in FIG. 2 emerge in left & right sides of the body which encode balance indications associated with left & right body tilts.

However, the present invention is based on a general sensory computer brain interface based on a patient specific communication library and is thus capable of relaying abstract information to the patient. Consequently, the patient can learn to relate sensory messages with virtually any kind of abstract balance-related information. In this context, the relayed messages or the communicated data are independent from body template, side, area, or type of sensation and thus constitute non-homologous embodiments of the present invention. In such non-homologous context, new relationships and correlations can be achieved in a way that, for instance, artificial sensations relating to road inclination are translated as graded sensations emergent between left index finger and left thumb as depicted in FIG. 5.

FIG. 5 depicts an exemplary embodiment where crucial information required to maintain balance on a non-even surface could be transferred in a non-homologous manner via activating sensory messages on the index finger and thumb. Abstract information such as an upward inclination 503 of a walking surface could be associated by the subject, after training, to sensations on the thumb 505. In a similar analogy, a down-ward inclination 502 can be communicated via artificial sensations on index finger and a flat surface 501, can be encoded via absence of artificial sensations.

The illustrated embodiment in FIG. 5, can also be realized such that artificial sensations are graded in relation to a quantitative aspect of terrain characteristics. This can be achieved, for instance, by varying the intensity or repetition rate of the artificial sensations with respect to the angle of upward or downward inclination. In such exemplary cases, the anatomical layout of target points of electrode-to-nervous-system interface locations (e.g. lumbar, thoracal and/or cervical spine) can be optimized by a submodule of the system to achieve an optimal level of communication across multiple independently-varied input channels. Homologous input (left-right tilt—left-right hand sensations) can here be combined with abstract sensations in thumb indicating upcoming incline on walking path 503.

FIGS. 6-8 illustrate various possible embodiments of balance prosthesis devices provided by the present invention.

FIG. 6 illustrates an exemplary balance prosthesis device according to an embodiment of the present invention. In this embodiment the balance prosthesis devices comprises an integrated neurostimulation module 610 (e.g. comprising a neuronal signal generator and an output amplifier) that is connected to a plurality of output signal leads that may be interfaced with a neurostimulation interface of the individual (e.g. a set of spinal cord stimulation electrodes or a DBS electrode). The balance prosthesis devices further comprises a communication antenna operably connected to a transceiver/sensor module 630, configured for wireless communication (e.g. via NFC, WIFI, Bluetooth or a similar wireless communication technology).

The transceiver/sensor module 630 is configured, for example, to receive one or more sensor signals from one or more sensors (as discussed above), indicative of a balance or equilibrium state of the individual. The transceiver/sensor module 630 is operably connected to a data/signal processing module 640 configured to generate one or more neurostimulation signals and/or signal parameters (e.g. waveform, pulse shape, amplitude, frequency, burst count, burst duration etc.) for generating the one or more neurostimulation signals. For instance the processing module 640 may access a data storage module 650 configured to store a plurality of relations, specific for the individual, associating a plurality of neurostimulation signals (or parameters used for generating a plurality of neurostimulation signals) with a plurality of corresponding balance indications, such as a medium intensity tingling sensation in the right hand associated with a medium degree of body tilt in the left direction.

The generated neurostimulation signal and/or the signal parameters are input into the integrated neurostimulation module 610 that may be configured to process (e.g. modulate, switch, amplify, covert, rectify, multiplex, phase shift, etc.) the one or more neurostimulation signals generated by the processing module 640 or to generate the one or more neurostimulation signals based on the signal parameters provided by the processing module 640.

The generated and processed neurostimulation signals are then output by the neurostimulation module 610 and can be applied to one or more electric contacts of a neurostimulation electrode (e.g. a DBS electrode or spinal cord stimulation electrode; not shown) via the output leads.

The balance prosthesis device may also comprise a rechargeable power source 660 that, for instance may be wirelessly charged via a wireless charging interface.

FIG. 7 illustrates a further exemplary balance prosthesis device according to an embodiment of the present invention. In this embodiment, the balance prosthesis device does not comprise an integrated neurostimulation module (see FIG. 6 above). Instead and similar as in the discussion for FIG. 1 above the data/signal processing module 740 is connected to a wireless transmitter module 710 that is connected to a wireless transmit antenna 770. The processing module 740 may be configured for generating one or more neurostimulation signals and/or signal parameters (e.g. waveform, pulse shape, amplitude, frequency, burst count, burst duration etc.) for generating the one or more neurostimulation signals. For instance the processing module 740 may access a data storage module 750 configured to store a plurality of relations, specific for the individual, associating a plurality of neurostimulation signals (or parameters used for generating a plurality of neurostimulation signals) with a plurality of corresponding balance indications.

The transmitter module 710 is configured for wireless communication (e.g. via NFC, Bluetooth, WIFI or a similar wireless communication technology) with a neurostimulation device of the individual (not shown; see FIG. 1). The transmitter module 710 may be configured to transmit the generated neurostimulation signal and/or the generated signal parameters to the neurostimulation device of the individual such as an IPG (see FIG. 1) that may be configured to process (e.g. modulate, switch, amplify, covert, rectify, multiplex, phase shift, etc.) the one or more neurostimulation signals received from the transmitter module 710 or to generate the one or more neurostimulation signals based on the signal parameters received from the transmitter module 710.

The balance prosthesis device may further comprise a wired receiver/sensor module 730 that is configured to receive/obtain one or more sensor signals from one or more sensors (as discussed above), indicative of equilibrium or balance state of the individual (e.g. gyroscope and accelerometer signals allowing the processing module to estimate the current or future body position of the individual with respect to a reference position). In the embodiment of FIG. 7 the sensor signals are not received by the sensor module wirelessly but are obtained via sensor signal leads. Naturally, wireless reception is also possible.

The neurostimulation device of the individual is configured to output and apply the generated and processed neurostimulation signals to one or more electric contacts of a neurostimulation electrode (e.g. a spinal cord stimulation electrode; not shown) to elicit the desired artificial sensory perception in the desired sensory cortex area. The balance prosthesis device 710 may also comprise a power source 760 that, for instance may be a removable battery.

FIG. 8 illustrates a further exemplary balance prosthesis device according to an embodiment of the present invention. In this embodiment, the balance prosthesis device comprises an integrated motions sensor, such as a 3-axis acceleration sensor 862 and a 3-axis gyroscope 864. In this case, balance indications can be determined and communicated to the individual (e.g. via two spinal cord stimulation leads) even without obtaining information from external sensor devices such as the wearable sensors discussed for FIG. 1.

FIG. 9 illustrates a scenario where a balance prosthesis device according to an embodiment of the present invention can be used to mitigate the effects of motion sickness (e.g. terrestrial motion sickness, space motion sickness and/or virtual reality motion sickness) by reinforcing the natural sense of balance of an individual 900 via an additional balance indication encoded via artificial sensory perceptions provided by the balance prosthesis. For instance, a person 900 on-board a ship 910 may experience a perceptual conflict between its visual and vestibular system, e.g. if the person 900 cannot see the horizon/waterline 900 and the ship 910 performs a combined roll, pitch and yaw movement.

In such situations, that may also occur in virtual reality environments the balance prosthesis device may transmit a balance indication 930 that helps to reinforce the correct balance perception 940 of the individual.

FIG. 10 illustrates the reciprocal situation where the person 1000 is not on-board the ship 1010 but controls the movement of the ship 1010 via a remote control terminal 1050 in this situation, sensor equipment on-board the ship transmit sensor signals indicative of the movement/balance state 1030 of the ship 1010 to a remote balance sensing device of the individual. The remote balance sensing device then provides a remote balance indication for the moving ship to the individual that is derived at least in part from the obtained sensor signals.

FIG. 11 illustrates another application scenario where a spinal cord stimulation (see FIG. 1 above) based remote balance sensing device supports a pilot 1100 in remotely piloting an unmanned aerial vehicle, e.g. via a conventional remote control or a brain computer interface remote control device.

The invention claimed is:

1. A balance prosthesis device for an individual, comprising:

a neurostimulation device of the individual, wherein the neurostimulation device is operably linked to one or more spinal cord electrodes implanted in the individual;

a sensor configured to obtain at least one sensor signal indicative of a balance or equilibrium state of the individual;

a processor operably connected to the sensor and configured to determine at least one neurostimulation signal based at least in part on the obtained sensor signal; and a transmitter operably connected to the processor and configured to transmit the at least one determined neurostimulation signal to the neurostimulation device;

wherein the neurostimulation device is configured to signal the one or more spinal cord electrodes to apply the at least one determined neurostimulation signal to directly stimulate afferent sensory axons of the central or peripheral nervous system of the individual targeting sensory neurons of the sensory cortex not directly associated with vestibulocortical pathways of the individual, wherein directly stimulating the afferent sensory axons elicits an artificial sensation in an area of the sensory cortex of the individual, and wherein signal parameters of the at least one determined neurostimulation signal are adjusted, based at least in part on one or more of the obtained sensor signal or at least one additionally obtained sensor signal, to elicit respective action potentials in respective sub-populations of the afferent sensory axons projecting to one or more of somatosensory neurons, auditory neurons, and visual neurons in respective areas of the sensory cortex to elicit the artificial sensation, wherein at least one of a perceived laterality or a location of the artificial sensation, elicited from directly stimulating the afferent axons, indicates a direction of a body tilt of the individual or a direction of a compensatory movement to decrease the body tilt, and wherein a perceived intensity of the artificial sensation, elicited from directly stimulating the afferent sensory axons, encodes an angle or a degree of the body tilt of the individual relative to at least one of a reference position, a range, an angle, or a degree of a compensatory movement to decrease the body tilt, and wherein the artificial sensation, elicited from directly stimulating the afferent sensory axons, provides a balance indication to the individual that is derived at least in part from the obtained sensor signal in order to support, mimic, substitute or enhance a natural sense of balance of the individual.

2. The balance prosthesis device of claim 1, wherein the at least one sensor signal comprises at least one motion sensor signal received from an accelerometer or gyroscope and obtained via a wired or wireless interface, and wherein the sensor obtains, via the wired or wireless interface, an auxiliary sensor signal originating from an auxiliary sensor device, wherein the auxiliary sensor device comprises as a camera, a light detection and ranging (LIDAR) sensor, a global positioning satellite (GPS) system, a pressure sensor or an elevation sensor.

3. The balance prosthesis device of claim 2, wherein the processor is further configured to:

detect, based at least in part on one or both of the at least one motion sensor signal and the auxiliary sensor signal using a trained machine learning system, whether a body of the individual is oriented at a degree of body tilt indicative of a risk to fall; and in response to said detection, generate a neurostimulation warning signal that is configured to elicit an artificial sensation in an area of the sensory cortex providing a falling warning to the individual.

4. The balance prosthesis device of claim 1, wherein the processor determines, based at least in part on the at least one motion sensor signal, one or more of:

an estimate of a current body position of the individual with respect to a reference body position; and an estimate of a future body position with respect to the reference body position.

5. The balance prosthesis device of claim 4, wherein the current and future body positions of the individual are characterized by one or more of the following parameters:

a body tilt of the individual in a coronal and/or a sagittal plane;

a rate of change of the body tilt of the individual in the coronal and/or the sagittal plane;

a deviation of a center of gravity of a body of the individual from a reference position or range for the center of gravity; and a rate of change of the deviation of the center of gravity from the reference position or range.

6. The balance prosthesis device of claim 1, wherein a perceived repetition rate of the elicited artificial sensation encodes a terrain characteristic comprising an inclination angle of a walking surface or a remaining distance to an obstacle.

7. The balance prosthesis device of claim 1, wherein a secondary sensory quality of the elicited artificial sensation comprises one or more of:

a texture of a somatosensation;

a color of a visual sensation; and a tone and timbre of an auditory sensation, and wherein the secondary sensory quality encodes body balance support information comprising an inclination of a walking surface or a remaining distance to an obstacle.

8. The balance prosthesis device of claim 1, wherein the at least one determined neurostimulation signal is synchronized with a walking pace of the individual to provide a continuous body tilt correction indication configured to improve a gait stability of the individual while walking.

9. The balance prosthesis device of claim 1, further comprising:

one or more implanted or wearable motion sensors configured to provide input signals to the sensor of the balance prosthesis device.

10. The balance prosthesis system of claim 9, further comprising:

one or more sensor devices providing further input signals to the sensor of the balance prosthesis device, wherein the one or more sensor devices comprise one or more of:

a camera device;

a LIDAR sensor device;

a GPS system;

a pressure sensor measuring the contact pressure between a foot of the individual and a walking surface; and at least two pressure sensors measuring a difference in contact pressure between two points on a walking surface to determine an inclination of the walking surface.

11. The balance prosthesis system of claim 9, further comprising:

a spinal cord stimulation device comprising a set of implanted spinal cord leads targeting somatosensory ganglions or afferent sensory nerve fibers within or adjacent to a spinal cord of the individual.

12. A method for providing a balance indication to an individual, the method comprising:

obtaining at least one sensor signal indicative of a balance or equilibrium state of the individual;

determining at least one neurostimulation signal based at least in part on the obtained sensor signal; and transmitting the at least one determined neurostimulation signal to a neurostimulation device of the individual, wherein the neurostimulation device is operably linked to one or more spinal cord electrodes implanted in the individual; and applying, via the one or more spinal cord electrodes and in response to being signaled by the neurostimulation device, the at least one determined neurostimulation signal to directly stimulate afferent sensory axons of the central or peripheral nervous system of the individual targeting sensory neurons of the sensory cortex not associated with vestibulocortical pathways of the individual, wherein directly stimulating the afferent sensory axons elicits an artificial sensation in an area of the sensory cortex of the individual, and wherein signal parameters of the at least one determined neurostimulation signal are adjusted, based at least in part on one or more of the obtained sensor signal or at least one additionally obtained sensor signal, to elicit respective action potentials in respective sub-populations of the afferent sensory axons projecting to one or more of somatosensory neurons, auditory neurons, and visual neurons in respective areas of the sensory cortex to elicit the artificial sensation;

wherein a perceived repetition rate of the artificial sensation, elicited from directly stimulating the afferent sensory axons, encodes a terrain characteristic comprising at least one of an inclination angle of a walking surface or a remaining distance to an obstacle, and wherein the artificial sensation, elicited from directly stimulating the afferent sensory axons, provides a balance indication to the individual that is derived at least in part from the obtained sensor signal in order to support, mimic, substitute or enhance a natural sense of balance of the individual.

13. The method of claim 12, wherein the at least one sensor signal is obtained via a wired or wireless interface from an accelerometer or a gyroscope, wherein the method further comprises:

obtaining, via the wired or wireless interface, an auxiliary sensor signal originating from an auxiliary sensor device, wherein the auxiliary sensor device comprises as a camera, a light detection and ranging (LIDAR) sensor, a global positioning satellite (GPS) system, a pressure sensor or an elevation sensor.

14. The method of claim 12, the method further comprising:

determining, based at least in part on the obtained sensor signal, one or more of:

an estimate of a current body position of the individual with respect to a reference body position; and an estimate of a future body position with respect to the reference body position, wherein the current and future body positions of the individual are characterized by one or more of the following parameters:

a body tilt of the individual in a coronal and/or a sagittal plane;

a rate of change of the body tilt of the individual in the coronal and/or the sagittal plane;

a deviation of a center of gravity of a body of the individual from a reference position or range for the center of gravity; and a rate of change of the deviation of the center of gravity from the reference position or range.

15. The method of claim 12, wherein a perceived laterality or location of the elicited artificial sensation indicates a direction of a body tilt of the individual or a direction of a compensatory movement to decrease the body tilt, and wherein a perceived intensity of the elicited artificial sensation encodes an angle or a degree of the body tilt of the individual relative to a reference position or range or an angle or degree of a compensatory movement to decrease the body tilt.

16. A non-transitory computer-readable storage device storing comprising program instructions which, when executed by a processor, cause a balance prosthesis device to:

obtain at least one sensor signal indicative of a balance or equilibrium state of an individual;

determine at least one neurostimulation signal based at least in part on the obtained sensor signal; and transmit the at least one determined neurostimulation signal to a neurostimulation device of the individual, wherein the neurostimulation device is operably linked to one or more spinal cord electrodes implanted in the individual; and apply, via the one or more spinal cord electrodes and in response to being signaled by the neurostimulation device the at least one determined neurostimulation signal to directly stimulate afferent sensory axons of the central or peripheral nervous system of the individual targeting sensory neurons of the sensory cortex area not associated with vestibulocortical pathways of the individual, wherein directly stimulating the afferent sensory axons elicits an artificial sensation in an area of the sensory cortex area of the individual, and wherein signal parameters of the at least one determined neurostimulation signal are adjusted, based at least in part on one or more of the obtained sensor signal or at least one additionally obtained sensor signal, to elicit respective action potentials in respective sub-populations of the afferent sensory axons projecting to one or more of somatosensory neurons, auditory neurons, and visual neurons in respective areas of the sensory cortex to elicit the artificial sensation;

wherein a perceived repetition rate of the artificial sensation, elicited from directly stimulating the afferent sensory axons, encodes a terrain characteristic comprising at least one of an inclination angle of a walking surface or a remaining distance to an obstacle, and wherein the artificial sensation, elicited from directly stimulating the afferent sensory axons, provides a balance indication to the individual that is derived at least in part from the obtained sensor signal in order to support, mimic, substitute or enhance a natural sense of balance of the individual.

17. The storage device of claim 16, wherein the at least one sensor signal is obtained via a wired or wireless interface from an accelerometer or a gyroscope, wherein the method further comprises:

obtaining, via the wired or wireless interface, an auxiliary sensor signal originating from an auxiliary sensor device, wherein the auxiliary sensor device comprises as a camera, a light detection and ranging (LIDAR) sensor, a global positioning satellite (GPS) system, a pressure sensor or an elevation sensor.

18. The storage device of claim 16, wherein the program instructions are further executable by the processor to cause the balance prosthesis device to:

determine, based at least in part on the obtained sensor signal, one or more of:

an estimate of a current body position of the individual with respect to a reference body position; and an estimate of a future body position with respect to the reference body position, wherein the current and future body positions of the individual are characterized by one or more of the following parameters:

a body tilt of the individual in a coronal and/or a sagittal plane;

a rate of change of the body tilt of the individual in the coronal and/or the sagittal plane;

a deviation of a center of gravity of a body of the individual from a reference position or range for the center of gravity; and a rate of change of the deviation of the center of gravity from the reference position or range.

19. The storage device of claim 16, wherein a perceived laterality or location of the elicited artificial sensation indicates a direction of a body tilt of the individual or a direction of a compensatory movement to decrease the body tilt, and wherein a perceived intensity of the elicited artificial sensation encodes an angle or a degree of the body tilt of the individual relative to a reference position or range or an angle or degree of a compensatory movement to decrease the body tilt.

20. The storage device of claim 16, wherein a secondary sensory quality of the elicited artificial sensation comprises one or more of:

a texture of a somatosensation;

a color of a visual sensation; and a tone and timbre of an auditory sensation, and wherein the secondary sensory quality encodes body balance support information comprising an inclination of a walking surface or a remaining distance to an obstacle.

* * * * *